(12) United States Patent
Li et al.

(10) Patent No.: US 11,858,965 B2
(45) Date of Patent: Jan. 2, 2024

(54) RECOMBINANT CELLULOSOME COMPLEX AND USES THEREOF

(71) Applicant: ACADEMIA SINICA, Taipei (TW)

(72) Inventors: Wen-Hsiung Li, Yilan County (TW); Anandharaj Marimuthu, Taipei (TW); Jui-Jen Chang, Taipei (TW); Yu-Ju Lin, Taipei (TW); Rizwana Parveen Rani Mohamed Gobil, Taipei (TW); Chieh-Chen Huang, Taichung (TW)

(73) Assignee: ACADEMIA SINICA, Taipei (TW)

( * ) Notice: Subject to any disclaimer, the term of this patent is extended or adjusted under 35 U.S.C. 154(b) by 23 days.

(21) Appl. No.: 17/327,514

(22) Filed: May 21, 2021

(65) Prior Publication Data

US 2021/0363196 A1 Nov. 25, 2021

Related U.S. Application Data

(60) Provisional application No. 63/029,295, filed on May 22, 2020.

(51) Int. Cl.
| | |
|---|---|
| C07K 14/195 | (2006.01) |
| C12P 7/06 | (2006.01) |
| C12P 19/02 | (2006.01) |
| C12N 9/42 | (2006.01) |
| C12N 9/02 | (2006.01) |
| C12P 19/14 | (2006.01) |

(52) U.S. Cl.
CPC .......... *C07K 14/195* (2013.01); *C12N 9/0069* (2013.01); *C12N 9/2437* (2013.01); *C12P 7/06* (2013.01); *C12P 19/02* (2013.01); *C12P 19/14* (2013.01); *C12Y 302/01004* (2013.01); *C07K 2319/00* (2013.01)

(58) Field of Classification Search
CPC .............. C07K 14/195; C07K 2319/00; C07K 2319/20; C07K 14/33; C12N 9/0069; C12N 9/2437; C12N 9/0006; C12N 9/0083; C12P 7/06; C12P 19/02; C12P 19/14; C12P 7/10; C12Y 302/01004; C12Y 101/99018; Y02E 50/10
See application file for complete search history.

(56) References Cited

U.S. PATENT DOCUMENTS 8,431,371 B2 * 4/2013 Li .................. C12Y 302/01006
435/320.1
9,340,794 B2 * 5/2016 Chang .................. C12N 15/815

OTHER PUBLICATIONS

Anandharaj et al., Constructing a yeast to express the largest cellulosome complex on the cell surface. PNAS., 2020, vol. 117 (5): 2385-2394; published Jan. 17, 2020. (Year: 2020).*

Broun et al., Catalytic plasticity of fatty acid modification enzymes underlying chemical diversity of plant lipids. Science, 1998, vol. 282: 1315-1317. (Year: 1998).*
Bule et al., Assembly of Ruminococcus flavefaciens cellulosome revealed by structures of two cohesin-dockerin complexes. Nature, Sci. Reports., 2017, vol. 7:759, pp. 1-14. (Year: 2017).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Usai et al., Clostridium cellulovorans metabolism of cellulose as studied by comparative proteomic approach. J. Proteomics, 2020, vol. 216, 103667, pp. 1-14. (Year: 2020).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Zhivin et al., Unique organization and unprecedented diversity of the Bacteroides (Pseudobacteroides) cellulosolvens cellulosome system. Biotechnol Biofuels, 2017, vol. 10:211, pp. 1-9. (Year: 2017).*
Ito et al., Improvement of Cellulose-Degrading Ability of a Yeast Strain Displaying Trichoderma reesei Endoglucanase II by Recombination of Cellulose-Binding Domains. Biotechnol. Prog., 2004, vol. 20: 688-691. (Year: 2004).*
Nakazawa et al., Hybrid Nanocellulosome Design from Cellulase Modules on Nanoparticles: Synergistic Effect of Catalytically Divergent Cellulase Modules on Cellulose Degradation Activity. ACS Catal., 2013, vol. 3: 1342-1348. (Year: 2013).*
Singh et al., Thermal unfolding and refolding of a lytic polysaccharide monooxygenase from Thermoascus aurantiacus†. RSC Adv., 2019, vol. 9: 29734-29742. (Year: 2019).*
Zamocky et al., Cloning, sequence analysis and heterologous expression in Pichia pastoris of a gene encoding a thermostable cellobiose dehydrogenase from Myriococcum thermophilum. Protein Expression and Purification, 2008, vol. 59: 258-265 (Year: 2008).*
Chang et al., "Biomimetic strategy for constructing Clostridium thermocellum cellulosomal operons in Bacillus subtilis," Biotechnol Biofuels, 2018, 11:157 (13 pgs.).
Currie et al., "Functional heterologous expression of an engineered full length CipA from Clostridium thermocellum in Thermoanaerobacterium saccharolyticum," Biotechnology for Biofuels, 2013, 6:32 (10 pgs).

(Continued)

*Primary Examiner* — Ganapathirama Raghu
(74) *Attorney, Agent, or Firm* — Prosyla Group PC (57) ABSTRACT

The present disclosure relates to a recombinant protein comprising a plurality of type II cohesin repeats. The present disclosure provides a recombinant cellulosome complex comprising: the recombinant protein comprising a plurality of type II cohesin repeats; a recombinant cellulosome complex integrating protein A comprising a plurality of type I cohesin repeats, a plurality of cellulose-binding modules and a type II dockerin; and a plurality of recombinant enzymes each comprising a type I dockerin. A cell, a method for digesting a cellulose and a method for producing ethanol are also provided.

16 Claims, 6 Drawing Sheets

Specification includes a Sequence Listing.

(56) References Cited

OTHER PUBLICATIONS

Fan et al., "Engineering yeast with bifunctional minicellulosome and cellodextrin pathway for co-utilization of cellulose-mixed sugars," Biotechnol Biofuels, 2016, 9:137 (11 pgs.).

Fan, et al., "Functional equivalence and evolutionary convergence in complex communities of microbial sponge symbionts," PNAS, Jun. 2012, pp. 109-118.

Huang et al., "Engineering microbial surfaces to degrade lignocellulosic biomass," Bioengineered, 2014, 5(2):96-106.

Kondo, A. and Ueda, M., "Yeast cell-surface display—applications of molecular display," Applied Microbiol Biotechnol, 2004, 64:28-40.

Lambertz et al., "Challenges and advances in heterologous expression of cellulolytic enzymes: a review," Biotechnol Biofuels, 2014, 7:135 (15 pgs.).

Lemaire et al., "OlpB, a New Outer Layer Protein of Clostridium thermocellum, and Binding of its S-Layer-Like Domains to Components of the Cell Envelope," Journal of Bacteriology, May 1995, 177(9):2451-2459.

Liang et al., "Engineered Pentafunctional Minicellulosome for Sumultaneous Saccharification and Ethanol Fermentation in *Saccharomyces cerevisiae*," Appl Environ Microbiol, Nov. 2014, 80(21):6677-6684.

Tang et al. "Efficient yeast surface-display of novel complex synthetic cellulosomes," Microb Cell Fact, 2018, 17:122 (13 pgs.).

Tsai et al., "Functional Display of Complex Cellulosomes on the Yeast Surface via Adaptive Assembly," ACS Synth Biol, 2013, 2:14-21.

Wen et al., "Yeast Surface Display of Trifunctional Minicellulosomes for Simultaneous Saccharification and Fermentation of Cellulose to Ethanol," Appl Environ Microbiol, Feb. 2010, 76(4):1251-1260.

\* cited by examiner

RECOMBINANT CELLULOSOME COMPLEX AND USES THEREOF

CROSS-REFERENCE TO RELATED APPLICATIONS

This application claims the benefit and priority to U.S. Provisional Application Ser. No. 63/029,295, filed May 22, 2020, the contents of which is incorporated herein in its entirety.

SEQUENCE LISTING

The instant application contains a Sequence Listing which is submitted electronically in .txt format and is hereby incorporated by reference in its entirety. The .txt copy, created on May 9, 2023, is named "G4590-08800US_SeqListing_20230509.txt" and is 1 kilobytes in size.

FIELD OF THE INVENTION

The present disclosure relates to a recombinant cellulosome complex and methods of use thereof.

BACKGROUND OF THE INVENTION

Cellulosomes from anaerobic bacteria are considered nature's finest cellulolytic machinery. Thus, many scientists have pursued the construction of a cellulosome in an industrial yeast. However, this remains highly challenging due to the size and complexity of cellulosomal genes.

In recent years, several groups of researchers have developed miniaturized versions of cellulosomes (called "mini-cellulosomes") on the *Saccharomyces cerevisiae* cell surface and demonstrated their cellulolytic and ethanol-producing abilities using microcrystalline cellulose (Wen et al. *Appl Environ Microbiol* 76, 1251-1260 (2010); Fan et al. *Proc Natl Acad Sci USA* 109 (2012); Tsai et al. *ACS Synth Biol* 2, 14-21 (2013); Liang et al. *Appl Environ Microbiol* 80, 6677-6684 (2014); Chang et al. *Biotechnol Biofuels* 11, 157 (2018); Currie et al. *Biotechnology for Biofuels* 6, 32 (2013); Fan et al. *Biotechnol Biofuels* 9, 137 (2016)). Enzymes in mini-cellulosomes displayed enhanced activity compared to free or immobilized enzymes (Huang et al. *Bioengineered* 5, 96-106 (2014)). However, a mini-cellulosome can accommodate only a few enzymes (12 so far), thus limiting the enzyme synergism. Engineering a large cellulosomal complex into the yeast genome remains highly challenging due to the multiple tandem repeats, lack of an effective stable chromosome integration strategy, low protein expression and secretion capability of the host (Tang et al. *Microb Cell Fact* 17, 122 (2018)). The existing strategies use episomal plasmids to express mini-cellulosomes for higher protein yields. However, the episomal expression also requires induction and constant selection, thus increasing production costs and raising stability concern (Lambertz et al. *Biotechnol Biofuels* 7, 135 (2014)).

Thus, there is a need for developing a highly efficient cellulolytic enzyme complex.

BRIEF SUMMARY OF THE INVENTION

A "superb enzyme complex" on a cell surface and a cellulolytic host is provided in the disclosure. The modified assembly of multiple enzymes in an engineered cellulosome complex facilitates enzyme synergism and exhibits a much greater degradation efficacy than the natural counterpart due to its highly ordered structural organization and assembly, which enables enzyme proximity synergy and enzyme-substrate-microbe complex synergy.

The present disclosure provides a recombinant protein comprising a plurality of type II cohesin repeats.

The present disclosure provides a recombinant cellulosome complex comprising:
the recombinant protein mentioned above;
a recombinant cellulosome complex integrating protein A comprising a plurality of type I cohesin repeats, a plurality of cellulose-binding modules and a type II dockerin; and
a plurality of recombinant enzymes each comprising a type I dockerin.

The present disclosure provides a cell expressing the recombinant protein or the recombinant cellulosome complex mentioned above.

The present disclosure provides a cell-culture comprising the cell mentioned above.

The present disclosure provides a method for digesting cellulose, comprising contacting cellulose with the pure culture, the cell, the recombinant protein, or the recombinant cellulosome complex mentioned above.

The present disclosure also provides a method for producing ethanol, comprising the method mentioned above.

The present disclosure is described in detail in the following sections. Other characteristics, purposes and advantages of the present disclosure can be found in the detailed description and claims.

DETAILED DESCRIPTION OF THE INVENTION

The present disclosure can be more readily understood by reference to the following detailed description of various embodiments of the disclosure, the examples, and the drawings and tables with their relevant descriptions. It is to be understood that unless otherwise specifically indicated by the claims, the disclosure is not limited to specific preparation methods, carriers or formulations, or to particular modes of formulating the extract of the disclosure into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "cellulosome" as used herein refers to a large bacterial extracellular multienzyme complex able to degrade crystalline cellulosic substrates.

The term "complex" as used herein means a coordination or association of components linked by chemical or biological interaction.

The term "recombinant polypeptide or "recombinant protein" can be used interchangable and refers to a polypeptide or protein produced by a host organism through the expression of a recombinant nucleic acid molecule, which has been introduced into said host organism or an ancestor thereof, and which comprises a sequence encoding said polypeptide or protein.

The term "genetic engineering" as used herein refers to a process by which genetic materials, including DNA and/or RNA, are manipulated in a cell or introduced into a cell to affect expression of certain proteins in said cell. Manipulation may include introduction of a foreign (or "exogenous") gene into the cell or inactivation or modification of an endogenous gene. Such a modified cell may be called a "genetically engineered cell" or a "genetically modified cell."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

A cellulosome is a highly efficient cellulolytic enzyme complex. Naturally, it is produced by *C thermocellum* and other anaerobic cellulolytic bacteria. The entire scaffold and all enzymatic subunits of the cellulosome are attached to a cell surface through a surface anchoring protein with cohesin-dockerin interaction. However, the efficiency and enzyme synergism of the cellulosome highly depends on the number of cohesin-dockerin interaction.

Accordingly, the present disclosure provides a recombinant protein comprising a plurality of type II cohesin repeats. In some embodiments of the disclosure, the recombinant protein comprises multiple tandem type II cohesin repeats that effectively and stably integrated in chromosome integration of a host cell, and is able to highly expressed and secreted.

All references cited herein are incorporated in their entirety. Specifically, exemplary cohesins, dockerins and GPI useful in accordance with various aspects and embodiments of the present disclosure are described in the references incorporated herein.

In some embodiments of the disclosure, the recombinant protein comprises 2, 3, 4, 5, 6, 7, 8, 9, 10, 11, or 12 type II cohesin repeats.

In some embodiments of the disclosure, the recombinant protein is obtained by modifying surface anchoring protein comprising the type II cohesin repeats. Examples of the surface anchoring protein include but are not limited to SdbA, Orf2p, or "outer layer protein B" (OlpB). Among the anchoring proteins, the OlpB typically includes seven Type II cohesins and can accommodate up to 63 cellulases in a cellulosome complex to form one of the largest known cellulolytic enzyme complexes.

In some embodiments of the disclosure, the recombinant protein is derived from *Clostridium thermocellum*.

In some embodiments of the disclosure, the recombinant protein further comprises an anchoring domain. Examples of the anchoring domain include but are not limited to a recombinant SLH anchoring domain or a recombinant glycosylphosphatidylinositol (GPI). For example, the SLH anchor domain is derived from *C. thermocellum* OlpB; the GPI is a cell surface protein from *S. cerevisiae*. The anchoring domain such as SLH anchoring domain or GPI in the recombinant protein is linked to a cell membrane-anchored protein.

In some embodiments of the disclosure, the codon of the recombinant protein is optimized according to a codon system utilized by the host.

In some embodiments of the disclosure, the recombinant protein is co-expressed with a recombinant cellulosome complex integrating protein A (CipA) comprising a plurality of type I cohesin repeats, a plurality of cellulose-binding modules (CBMs) and a type II dockerin.

Accordingly, the present disclosure provides a recombinant cellulosome complex comprising:
 the recombinant protein mentioned above;
 a recombinant cellulosome complex integrating protein A comprising a plurality of type I cohesin repeats, a plurality of cellulose-binding modules and a type II dockerin; and
 a plurality of recombinant enzymes each comprising a type I dockerin.

The CBM as used herein binds cellulosic substrates. A cellulosomal enzyme contains a type I dockerin, which interacts with the type I cohesin of CipA. The type II dockerin binds to the type II cohesin repeats in the recombinant protein. In some embodiments of the disclosure, the recombinant cellulosome complex is derived from *Clostridium thermocellum*. A typical *C. thermocellum* cellulosome is comprised of a central non-enzymatic scaffold subunit known as "cellulosome integrating protein A" (CipA) with nine Type I cohesins (Kruus et al. *Proceedings of the National Academy of Sciences* 92, 9254-9258 (1995)).

In some embodiments of the disclosure, the recombinant cellulosome complex integrating protein A comprises 2, 3, 4, 5, 6, 7, 8, 9, 10, 11, or 12 type I cohesin repeats. In some embodiments of the disclosure, the recombinant cellulosome complex integrating protein A comprises 3, 6, or 9 type I cohesin repeats.

In some embodiments of the disclosure, the recombinant cellulosome complex integrating protein A comprises 2, 3, 4, or 5 cellulose-binding modules. In some embodiments of the disclosure, the recombinant cellulosome complex integrating protein A comprises two cellulose-binding modules.

It is believed, though not intended to be restricted by any theoretical, that the cohesin-dockerin interaction of a cellulosome facilitates spatial proximity among various cellulases (proximity effect) and the cellulose-binding capacity of CBM enhances cellulose utilization (targeting effect) (Blumer-Schuette et al. *FEMS Microbiology Reviews* 38, 393-448 (2014)). These advantages provide clues for developing an efficient way to elevate the saccharification of cellulosic substrates (Schwarz, *Applied Microbiology and Biotechnology* 56 (2001)).

In some embodiments of the disclosure, the recombinant protein is co-expressed with a plurality of recombinant enzymes each comprising a type I dockerin. In some embodiments of the disclosure, the recombinant enzymes are cellulolytic enzymes. In some embodiments of the disclosure, the cellulolytic enzymes are endoglucanases, exoglucanases or β-glucosidases.

In one some embodiment of the disclosure, the recombinant protein is co-expressed with a recombinant oxidative enzyme. In some embodiments of the disclosure, the recombinant oxidative enzyme is a lytic polysaccharide monooxygenase (LPMO). In some embodiments of the disclosure, the recombinant protein is co-expressed with a recombinant cellobiose dehydrogenase (CDH).

It is believed, though not intended to be restricted by any theory, that the conversion of cellulose into simple sugars requires at least three types of enzymes: endoglucanases (EGs), exoglucanases (CBHs) and beta-glucosidases (BGSs) (Lambertz et al. *Biotechnol Biofuels* 7, 135 (2014)). Apart from these hydrolases, recent studies have reported a new class of oxidative enzymes, called lytic polysaccharide monooxygenases (LPMO), which can efficiently degrade the crystalline cellulose and increase the soluble sugar released by 2.6-fold (Arfi et al. *Proc Natl Acad Sci USA* 111, 9109-9114 (2014)). Hence, LPMO was named "cellulase booster". It requires an enzyme-copartner, called cellobiose dehydrogenase (CDH), which donates the electron required by LPMO for its activity. Therefore, three types of fungal cellulases were selected—endoglucanase (TrEgIII), exoglucanase (CBHII) and β-glucosidase (NpaBGS), and also selected were the cellulase booster (TaLPMO) and its enzyme-copartner (MtCDH), which were then fused with Type I dockerin of *C. thermocellum* to facilitate the cellulosomal integration.

In one embodiment of the disclosure, adding LPMO and CDH to the cellulase mixture greatly increased the soluble sugar release. Yeast cells generally utilize the glucose released from hydrolysis, and the addition of methylglyoxal inhibits the host's glucose metabolism. With this method, the amount of glucose released during hydrolysis could be quantified readily. The glucose amount is low without the addition of methylglyoxal, due to the immediate uptake of glucose by the cells. In contrast, the co-culture of the enzyme host and the scaffold host accumulate a higher amount of glucose in the presence of methylglyoxal. These results confirm that the cellulosome has stronger cellulolytic activity on higher order celluloses, i.e., avicel. In some embodiments of the disclosure, to achieve efficient secretion and cellulosome assembly, the cellulosomal genes (i.e., CipA and OlpB) and dockerin-fused enzymes are engineered into two different hosts. The cell consortium approach was adopted and the ratio of each host was controlled according to the complexity of the cellulosic substrates to achieve a higher ethanol titer.

In one embodiment of the disclosure, the recombinant protein is expressed by a cell. In some embodiments of the disclosure, the recombinant protein is expressed on the surface of the cell. In one embodiment, the cell is a yeast cell; in a further embodiment, the yeast cell is *Kluyveromyces marxianus*. *K. marxianus* has several advantages over *S. cerevisiae* and other yeast strains, including faster growth, higher thermotolerance, pentose sugar fermentation and higher secretion capacity (Chang et al. *Biotechnology for Biofuels* 5, 53 (2012); Chang et al. *Biotechnology for Biofuels* 6, 19 (2013); Chang et al. *Applied Energy* 132, 465-474, (2014)). It is Crabtree-negative, thermotolerant (up to 46° C.) and capable of fermenting various sugars, including pentose sugars (i.e., xylose, arabinose, and inulin) (Fonseca et al. *Applied Microbiology and Biotechnology* 79, 339-354 (2008); Lertwattanasakul et al. *Biotechnology for Biofuels* 8, 47, (2015)). *K. marxianus* grows faster than *S.* cerevisiae and other yeasts (Lee et al. *Sci Rep* 8, 7305 (2018); Banat et al. *World J Microbiol Biotechnol* 8, 259-263 (1992); Ho et al. *Applied Energy* 100, 27-32, (2012)). Moreover, the secretory capacity of *K. marxianus* is higher than that of *S. cerevisiae* due to its efficient signal peptides (Fonseca et al. *Applied Microbiology and Biotechnology* 79, 339-354 (2008)). Finally, *K. marxianus* is a GRAS (generally regarded as safe) and QPS (qualified presumption of safety) certified organism (Spencer et al. *Appl Microbiol Biotechnol* 58, 147-156 (2002)). These attributes make *K. marxianus* an excellent host for industrial applications (Chang et al. *Applied Energy* 132, 465-474 (2014)).

In one embodiment of the disclosure, the recombinant protein, recombinant cellulosome complex, recombinant enzymes or recombinant oxidative enzyme are encoded by the genome of a cell.

In one embodiment of the disclosure, the CipA gene (with 9 Type I cohesin repeats) and the largest OlpB gene (with 7 Type II cohesin repeats) are synthesized. The multiple repeats in the cohesins of CipA and OlpB genes make it extremely difficult for their cDNA cloning or even DNA synthesis. This problem was overcome by randomizing the codons in the repeats and synthesizing CipA and OlpB genes. In one embodiment of the disclosure, these two genes were then integrated into the *K. marxianus* genome.

In one embodiment, the recombinant cellulosome complex is expressed by a cell. In one embodiment, the recombinant cellulosome complex is expressed on a surface of the cell. In one embodiment of the disclosure, the cell is a yeast cell. In one embodiment, the yeast is *Kluyveromyces marxianus*.

The present disclosure provides a cell expressing the recombinant protein or the recombinant cellulosome complex described herein.

In one embodiment of the disclosure, the cell expresses the recombinant protein or the recombinant cellulosome complex on the surface of the cell. In one embodiment, the cell is a yeast cell. In one embodiment, the yeast is *Kluyveromyces marxianus*.

The present disclosure provides a cell-culture comprising the cell described herein.

The present disclosure provides a method for digesting a cellulose, comprising the cell, the recombinant protein, or the recombinant cellulosome complex described herein.

In one embodiment of the disclosure, the cellulose is a microcrystalline cellulose.

In one embodiment, the method is for converting the cellulose into reducing sugars and/or ethanol.

The present disclosure also provides a method for producing ethanol, comprising the method described herein.

The present disclosure provide exemplary methods and composition embodiments that overcame these difficulties by designing and synthesizing the scaffold gene (CipA) and the anchoring protein gene (OlpB) using synthetic biology techniques. The engineered *Kluyveromyces marxianus*, a probiotic yeast, secreted a cocktail of cellulolytic enzymes, including cellulases, a cellulase booster and its co-enzyme. It was shown that both the number of enzyme-binding sites and the number of cellulose-binding modules in the cellulosome improve its ethanol production rate. The largest cellulosome of the present disclosure can accommodate many enzymes, whereas previously the largest engineered cellulosome could accommodate only few enzymes and was in a plasmid, not in the yeast genome. The present engineered host released higher quantities of ethanol from cellulosic substrates than any previously constructed yeast cellulosome. The engineered cellulosomal yeast strains efficiently converted the microcrystalline cellulose into reducing sugars and/or ethanol and are suitable for consolidated bioprocessing (CBP).

The performance of the present construct is not dramatically higher than that of conventional construct, but it used genome integration, instead of using an episomal plasmid, which has the advantage of increasing the gene copy number in the yeast cell, but it is not stable in the absence of selection markers.

The following examples are provided to aid those skilled in the art in practicing the present disclosure.

Examples

Methods

Strains and Media

*Escherichia coli* strain DH5a was used as the host for plasmid construction and propagation. *E. coli* strain JM110 was used to demethylate plasmid and to ligate large DNA fragments. *E. coli* strains were cultured in Luria-Bertani (LB) medium (10 g/L tryptone, 5 g/L yeast extract, and 10 g/L NaCl) supplemented with 50 µg/mL ampicillin. Yeast *Kluyveromyces marxianus* 4G5 strain was used to develop a CBP host, which was maintained in YPG medium (1% yeast extract, 2% peptone, 2% galactose) and cultured at 30° C. at 300 rpm. Yeast transformants were cultured in YPG media supplemented with either G418 or hygromycin B at a concentration of 200 µg/mL.

Cellulosomal Construct Design and Synthesis

Scaffolds (CipA) were designed in a biomimetic manner using the *C. thermocellum* CipA gene as a backbone, which has nine Type I cohesins with a CBM. The original CipA was named CipA 1B9C since it has one CBM (B) and nine cohesins (C). Similarly, synthetic scaffolds CipA 1B6C and CipA 1B3C were designed by removing the cohesins 6-9 and 4-9, respectively. The synthetic scaffold CipA 2B9C was designed by adding one more CBM between cohesin 7 and 8, while CBM was removed to form CipA 0B9C. The anchoring protein (OlpB) mimics the *C. thermocellum* OlpB, which contains seven Type II cohesins with a SLH anchoring domain and a long tandem repeat (TR). The SLH domain was replaced with the ScGPI domain and the TR domain was removed to avoid the synthesis constraints. All the constructs were codon optimized and difficult sequences were randomized using the Build Optimization Software Tools (BOOST) developed by DOE-Joint Genome Institute (JGI), USA (Oberortner et al. *ACS Synthetic Biology* 6, 485-496 (2017)). All of the constructs were synthesized and inserted into the yeast integration plasmid pKLac2-α-Kan using AvrII and NotI.

EgIII and NpaBGS genes were obtained from previous studies (Chang et al. *Biotechnology for Biofuels* 5, 53 (2012); Chen et al. *Biotechnology for Biofuels* 5, 24 (2012)). The CBHII (KC311337), LPMO and CDH genes were chemically synthesized by GenScript Inc. (Piscataway, NJ, USA) and codon-optimized for *K. marxianus* expression (Chang et al. *Biotechnology for Biofuels* 6, 19 (2013)). To fuse the C-terminal dockerin each cellulase gene was amplified with gene-specific primers using High-Fidelity DNA polymerases (New England Biolabs), digested with AvrII and SpeI and inserted into the yeast integration plasmid pKLac2-α-Kan-DocT-kit, which carries a Type I dockerin.

Yeast Transformation and Clone Screening

*K. marxianus* cells were cultured in 5 mL YPG medium at 30° C. at 300 rpm for 16 h. Yeast competent cells were prepared as described in Chang, et al. (Chang et al. *Biotechnology for Biofuels* 5, 53 (2012)). SacII digested gene cassettes (1 µg) were electroporated (1.0 kV, 400Ω, and 25 µF capacitance) with 40 µl of competent cells, in a BioRad system (Gene Pulser Xcell™ Bio-Rad, Hercules, CA) with an aluminum cuvette (2 mm). Then, electroporated cells were recovered at 30° C. for 3 h and plated onto YPG plates supplemented with G418 or hygromycin B (200 µg/mL). Transformed yeast colonies were mixed with QuickExtract™ DNA Extraction Solution (EPICENTRE, Madison, Wisconsin) to remove the cell wall, and were used as a template for PCR verification. Chromosomal integration of each gene was confirmed by the PCR reaction using gene-specific primers and the stability was verified up to five generations.

Cellulosome Assembly

The complex formation of dockerin-fused cellulases and scaffolds were confirmed by native polyacrylamide gel electrophoresis (Native-PAGE). Briefly, culture supernatants of cellulases, scaffold and anchoring protein hosts were collected after 48 h cultivation at 37° C. at 300 rpm. Then, supernatants were condensed 50-fold using Vivaspin 20 (10-kDa cutoff, Merck Millipore, USA) and complex formation was performed by mixing each supernatant at different ratios, incubated for 2 h at 37° C. without shaking. After incubation, the enzyme mixture was loaded onto native-PAGE (stacking gel-5%; separating gel-8%) with 2×sample loading dye (without SDS). The same sample was heated at 100° C. and loaded onto 8% SDS-PAGE (Arfi et al. *Proc Natl Acad Sci USA* 111, 9109-9114 (2014); Morais et al. Deconstruction of Lignocellulose into Soluble Sugars by Native and Designer Cellulosomes. mBio 3, (2012)).

Immunofluorescence microscopy and FACS.

Immunostaining was performed using the method described in Chang, et al. (Chang et al. *Biotechnol Biofuels* 11, 157 (2018)). Yeast cells expressing anchoring protein was collected ($A_{600}$ of 1.0) and washed three times with PBS (pH 7.4). Cells were resuspended in 4% paraformaldehyde (PFA) and incubated for 30-60 min at 4° C. Then, cells were centrifuged and washed with PBS buffer to remove the excess PFA and resuspended in 500 µL of bovine serum albumin (BSA, 1 mg/mL in PBS) containing 0.5 µg of anti-FLAG primary antibody (Biotools, Taiwan) and incubated for 3 h. The cells were harvested by centrifugation and resuspended in 500 of PBS containing secondary antibody conjugated with DyLight™405 fluorophores (Jackson Immunoresearch, USA) and incubated for 1 h. After incubation, the cells were washed three times and 2 µL of cell suspension were fixed on a slide and observed under Leica TCS SP5 II confocal microscopy (Wetzlar, Germany). Similarly, immunostained yeast cells were subjected to FACS analysis to further confirm the anchoring efficiency. Approximately 50,000 cells were used for the analysis using MoFlo™ XDP Flow Cytometer (Beckman Coulter, Inc., CA, USA).

Real-Time Quantitative PCR

Total RNA was isolated from the transformants using AccuPure Yeast RNA mini Kit in the iColumn automated system (iColumn12, AccuBioMed, Taiwan). cDNA synthesis was conducted using a reverse transcription kit (SuperScript™ II kit, Invitrogen, USA). The relative quantification of each gene was carried out using gene-specific Universal Probe Library probes (LightCycler W480 Probes Master, Roche) with a specific primer pair (amplicon size around 100 to 150 bp) on a LightCycler (LightCycler 480, Roche). The actin gene was used as the reference gene and each analysis was repeated three times. The relative expression level was calculated using the $2^{-\Delta\Delta Ct}$ method (Livak & Schmittgen. *Methods* 25, 402-408 (2001)).

Enzyme Assays

Enzyme activity was assayed as described in Chang, et al. (Chang et al. *Biotechnology and Bioengineering* 115, 751-761 (2018)). The activity of dockerin-fused cellulases was determined by various assays using specific substrates. Endo-glucanase (EgIII-t) activity was measured using dye-CMC (Megazyme, Wicklow, Ireland) as a substrate. The 100 µL assay reaction contains 40 µL of condensed supernatants with 60 µL of buffer solution (0.4% (w/v) dye-CMC, 50 mM sodium acetate, pH 5), incubated at 40° C. for 6 h. After incubation, 250 µL precipitation solution was added, centrifuged at 8000 rpm for 10 min and absorption was measured at 590 nm. Similarly, exo-glucanase (CBHII-t) activity was estimated using PASC. The assay was performed by adding 100 µL of supernatants with 900 µL buffer solution containing 50 mM sodium acetate (pH 5), 0.4% PASC and incubated in Thermal Shaker at 40° C. for 12 h. The released reducing sugars were measured by the dinitrosalicylic acid (DNS) method and sugar concentration was calculated using glucose standard (Ghose, T. K. in *Pure and Applied Chemistry* Vol. 59, 257 (1987)). β-glucosidase (NpaBGS-t) activity was determined by the formation of p-Nitrophenol from the hydrolysis of substrate p-Nitrophenyl-3-D-glucuronide (pNPG) and absorption was measured at 410 nm. Total cellulase activity was determined using filter paper as the substrate and the reducing sugar release was estimated by the DNS method.

Fermentation and Ethanol Production

The yeast cells expressing cellulases, scaffold and anchoring proteins were cultured and washed twice with YP medium (1% yeast extract, 2% peptone, 10 mM $CaCl_2$)). Then, 20 O.D. cells ($A_{600}$) were resuspended in YP media, supplemented with 0.042% Tween 80, 1% Avicel or PASC. In sugar release experiment, 100 mM methylglyoxal was added to the media to inhibit the glucose metabolism of the host. Fermentation was carried out in an anaerobic 50 mL serum tube with 5% volumetric headspace and incubated for several days at 37° C. with agitation at 300 rpm (Chang et al. *Biotechnology for Biofuels* 6, 19 (2013)). The ethanol and glucose concentrations were analyzed using High-performance liquid chromatography (HPLC) (Jasco PU-2089 Quaternary HPLC PUMP, JASCO International Co., Ltd., Japan) coupled with the ICSep ICE-COREGEL 87H3 Column (Transgenomic, USA) and Shodex RI-101 Refractive Index Detector (RID) (ECOM, Czech Republic).

Homology Modeling of Dockerin-Fused Enzymes

To predict the three-dimensional structures of dockerin-fused enzymes, the protein sequence was blasted against the protein data bank (PDB) database. The online software Protein Homology/analogY Recognition Engine V 2.04 (Phyre2) (Kelley et al. *Nature Protocols* 10, 845 (2015)) and RaptorX (Milberg et al. *Nature Protocols* 7, 1511 (2012)) were used to predict the homology model of each enzyme. Bumps present in the predicted model were removed and missing side chains were added using the "WHAT IF Web Interface". The predicted protein structure was validated using a protein structure validation (PSVS) tool. A Ramachandran plot was used to analyze the structure quality. The modeled protein structures were visualized and images were rendered using UCSF-Chimera software (Pettersen et al. *J Comput Chem* 25, 1605-1612 (2004)).

Statistical Analysis

All the experiments were performed in triplicate and results were expressed as means±standard deviations (SD). Statistical significance was analysed using two-tailed student t-tests (with unequal variance) in Microsoft Excel 2016. P<0.05 was considered statistically significant throughout the study.

Results

Design and Synthesis of Cellulosomal Scaffolds

Figure 1:
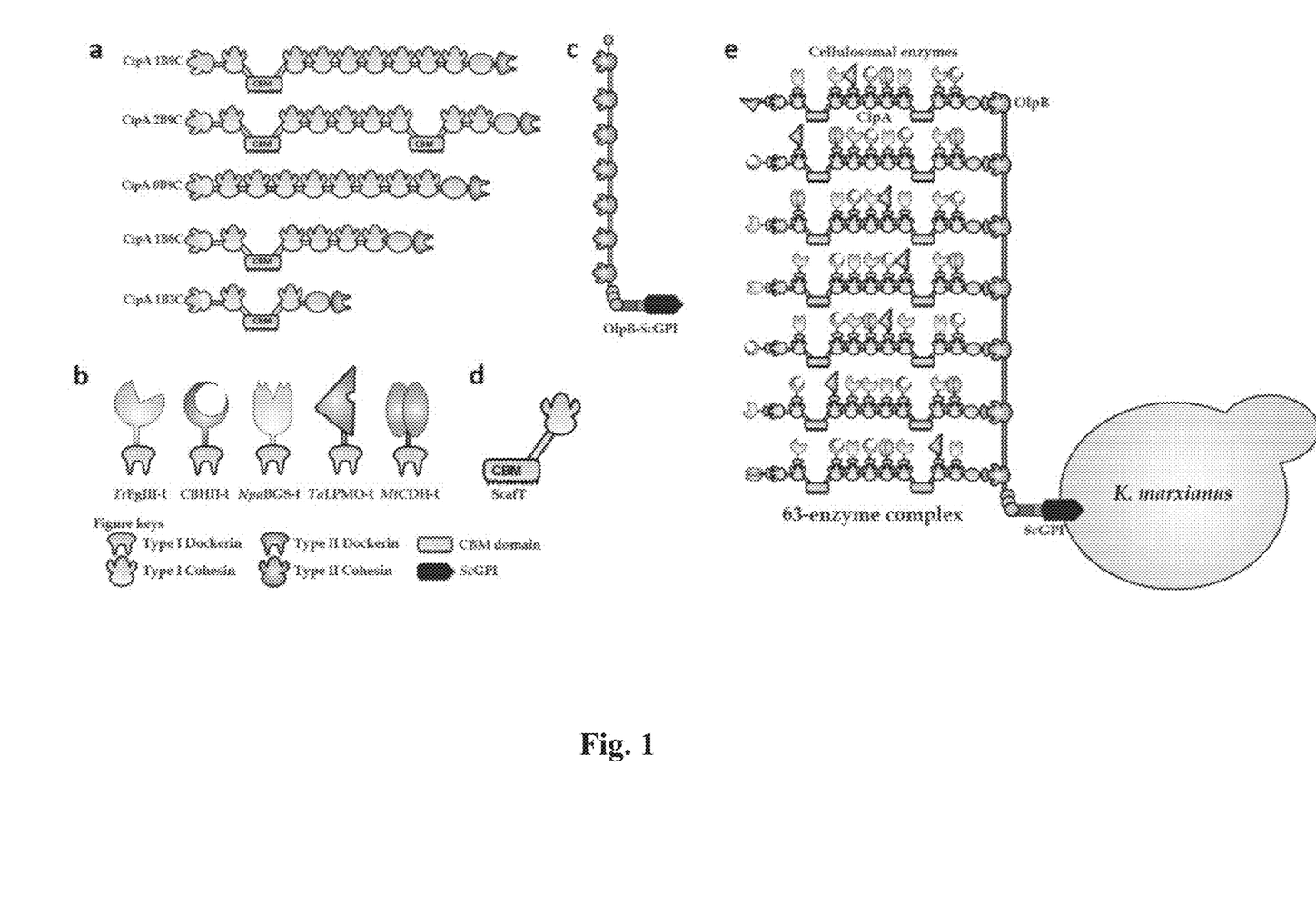
FIG. 1. Schematic representation of cellulosomal proteins. (a) Biomimetic scaffold (CipA) with varying numbers of cohesins and cellulose-binding modules (CBMs). In a scaffold name, "B" represents the number of CBMs and "C" represents the number of cohesins. For example, CipA1B9C means that 1 CBM and 9 cohesions are present in a CipA. (b) Outer layer scaffold protein B (OlpB) with 7 Type II cohesins and the ScGPI cell surface anchor. (c) Fungal cellulases fused with dockerin T. (d) ScafT containing a CBM and a cohesin T. (e) Schematic diagram of the engineered cellulosome complex with 63 enzymes on the cell surface of *K. marxianus*.

Several components were designed and synthesized to engineer an entire cellulosome system into the yeast genome (see Methods). A synthetic scaffold was designed according to the sequence of the CipA gene (5.6 kb) in *C. thermocellum* ATCC 27405 (CP000568). To evaluate the effect of cohesin number, three synthetic scaffolds containing 3, 6 and 9 cohesins with a single CBM (denoted 1B3C, 1B6C, and 1B9C) were designed. Similarly, to examine the effect of CBMs on cellulose-binding, two more synthetic scaffolds were designed with no or two CBMs (0B9C and 2B9C) (FIG. 1a).

An anchoring protein plays a critical role in the attachment of the cellulosome complex to the yeast cell surface. However, the anchoring domain of *C. thermocellum* is not suitable for a eukaryotic host. Therefore, the anchoring efficiency of glycosylphosphatidylinositol (ScGPI), a cell surface protein from *S. cerevisiae*, on *K. marxianus* (Kondo & Ueda. *Applied Microbiology and Biotechnology* 64, 28-40 (2004)) was tested. The pKlac2 plasmid containing ScGPI fused with a green fluorescent protein (GFP) and a 12×His was expressed in *K. marxianus* and its anchoring efficiency was confirmed by fluorescence microscopic analysis. The imaging data showed a successful display of ScGPI on the *K. marxianus* cell surface. Then the largest cell surface scaffold was designed using OlpB as the backbone (see Methods). The seven Type II cohesins of OlpB were selected and the original anchoring domain (SLH) was replaced with the ScGPI domain to facilitate surface display. OlpB contains long tandem repeats (TRs) with highly repetitive TPSDEP (SEQ ID NO: 1) amino acid sequences (Lemaire et al. *Journal of Bacteriology* 177, 2451-2459 (1995)). In view of the repetitiveness of the OlpB DNA sequences, the TR length was reduced and 7 cohesins were directly fused with the trimmed TRs and with the ScGPI domain (FIG. 1c). For efficient translation in *K. marxianus*, both CipA and OlpB gene sequences were codon optimized for *K. marxianus* and the repeats in the cohesins were randomized to avoid DNA synthesis constraints.

Conversion of Free Cellulases into Cellulosomal Mode

As fungal cellulases have no dockerin, two kinds of dockerin fusion kits were designed according to the Type I dockerin of *C. thermocellum* (DocT). Based on the domain organization of each enzyme, the dockerin module was fused at either the N- or C-terminus. A 36 bp glycine-rich linker was used between the dockerin module and the catalytic domain to avoid the conformational changes due to dockerin fusion (Arfi et al. *Proc Natl Acad Sci USA* 111, 9109-9114 (2014)) and an 8×His tag was fused for purification and detection purposes (see Methods). For efficient secretion of each cellulase into the medium, the native secretory signal peptide (α-mating type) of *Kluyveromyces lactis* was fused at the N-terminus. In the previous studies, several fungal cellulases in *K. marxianus*, including TrEgIII, CBHII and NpaBGS (Chang et al. *Biotechnology for Biofuels* 6, 19 (2013); Chang et al. *Biotechnology and Bioengineering* 115, 751-761 (2018)) were successfully expressed. In this study, along with cellulases, cellulase boosters LPMO (from *Thermoascus aurantiacus*, TaLPMO) and CDH (from *Myceliophthora thermophila*, MtCDH) were also included. To convert the free fungal cellulases into the cellulosomal mode, DocT was fused at either the N- or C-terminus of TrEgIII, CBHII and NpaBGS. Surprisingly, CBHII and TrEgIII retained their activity after C-terminus dockerin fusion but not after N-terminus dockerin fusion. However, the enzyme activity was recovered after adding a ScafT. On the other hand, NpaBGS displayed similar amounts of enzyme activity in either N- or C-terminal dockerin fusion. Based on a previous study (Arfi et al. *Proc Natl Acad Sci USA* 111, 9109-9114 (2014)), a dockerin was fused at the C-termini of TaLPMO and MtCDH, since the N-terminal histidine residue has been evolutionarily conserved in LPMO and is essential for its function. Three-dimensional protein structures of dockerin-fused chimeric enzymes were predicted using homology modeling, and the results showed that the dockerin fusion did not alter their substrate-binding pockets.

Genome Integration of Cellulosomal Genes

The cellulosomal genes were integrated into the Lac4 region of the *K. marxianus* 4G5 genome using yeast integration plasmid pKLac2. To study the effect of cohesin numbers and CBMs on crystalline cellulose, five different CipA variants-CipA1B3C, 1B6C, 1B9C, 2B9C, and 0B9C-were transformed individually into *K. marxianus* 4G5 (see Online Methods). The chromosomal integration was confirmed by PCR verification, and their expression was confirmed by Western blot (WB) analysis using anti-His antibody. The WB results of CipA1B3C showed a distinctive band at ~89 kDa. Similarly, transformants expressing 1B6C, 1B9C, 0B9C and 2B9C displayed bands at ~142 kDa, ~194 kDa, ~172 kDa and ~217 kDa, respectively. Finally, the anchoring host (AH) was developed by transforming OlpB-ScGPI into the *K. marxianus* 4G5 genome, and their expression was confirmed by WB analysis and a band was observed at ~211 kDa.

Demonstration of OlpB Cell-Surface Display Using Immunofluorescence Analysis

Figure 2:
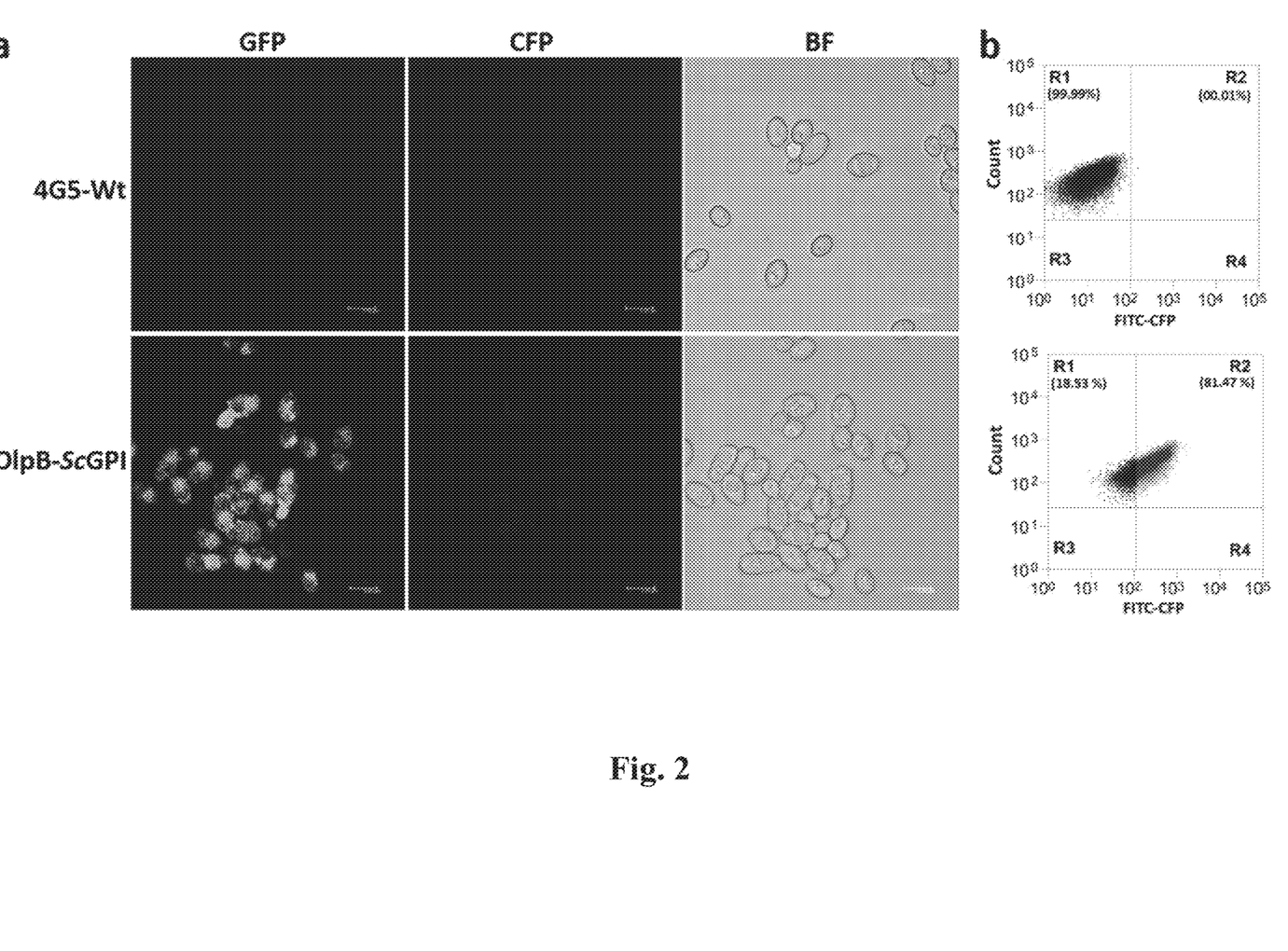
FIG. 2. Confirmation of OlpB-ScGPI anchoring on the cell surface. (a) Anchoring of OlpB-ScGPI on the *K. marxianus* cell surface confirmed by immunostaining and confocal microscopy using GFP or CFP. (b) Fluorescence-Activated Cell Sorting analysis of immunostained cells expressing OlpB-ScGPI.

Anchoring of the entire OlpB-ScGPI on the cell surface was confirmed by immunofluorescence microscopy and Fluorescence-Activated Cell Sorting (FACS) analysis (see Methods). The yeast cells expressing OlpB protein exhibited a strong green fluorescence signal throughout the cell, making it hard to distinguish the protein anchored on the cell surface from the internal OlpB protein. Since the monoclonal antibodies did not penetrate the yeast cell wall, the yeast cells expressing OlpB protein were immuno-stained with DyeLight-405 secondary antibody conjugated with cyan fluorescence protein (CFP). A clear blue fluorescence was observed around the anchoring host, thus confirming that the OlpB protein was successfully displayed on the *K. marxianus* cell surface, whereas no fluorescence was observed on wild-type strains (FIG. 2a). Similarly, FACS analysis was performed using 50,000 cells expressing the OlpB protein, among which 81.47% showed a fluorescence signal, further confirming the anchoring of OlpB on the cell surface (FIG. 2b).

Cellulosome Complex Formation

Figure 3:
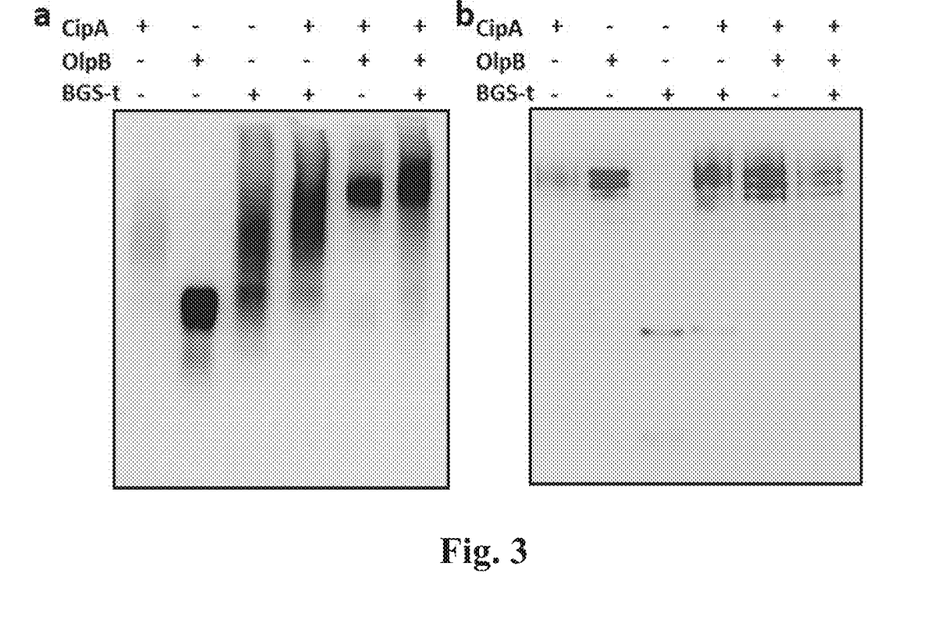
FIG. 3. Cellulosome complex formation analysis. Condensed supernatants of CipA1B9C, OlpB-ScGPI and NpaBGS-t were mixed together in different molar ratios and allowed to form complexes at 37° C. with 10 mM $CaCl_2$). (a) Native-PAGE analysis. (b) SDS-PAGE analysis.

The cellulosome complex assembly was demonstrated using the supernatants of CipA1B9C, BGS-t and cell extract of OlpB-ScGPI. They were allowed to form complexes at 37° C. and were analyzed using native- or SDS-PAGE followed by Western blot analysis. In native-PAGE WB, a shift in the band was observed and thus confirmed that the cellulosome complex had been formed (FIG. 3a). A smear of the band in the BGS-t lane was observed, which might be due to the N-glycosylation of the DocT domain. As expected, the Type I dockerin of BGS-t bound randomly to the available nine Type I cohesins of CipA scaffold and shifted the band upward. Similarly, the Type II dockerins of CipA interacted with the Type II cohesins of OlpB-ScGPI and formed a complex. When mixing the three components together, a clear band was observed at the top of the lane, thus confirming the assembly of all three components to form cellulosomes. The cellulosome complex was dissociated by heating to 100° C., and separated bands were observed on SDS-PAGE (FIG. 3b). These data confirm that the N-glycosylation of CipA and enzymes did not affect their ability to form cellulosomes.

Constructing Enzyme Hosts

Figure 4:
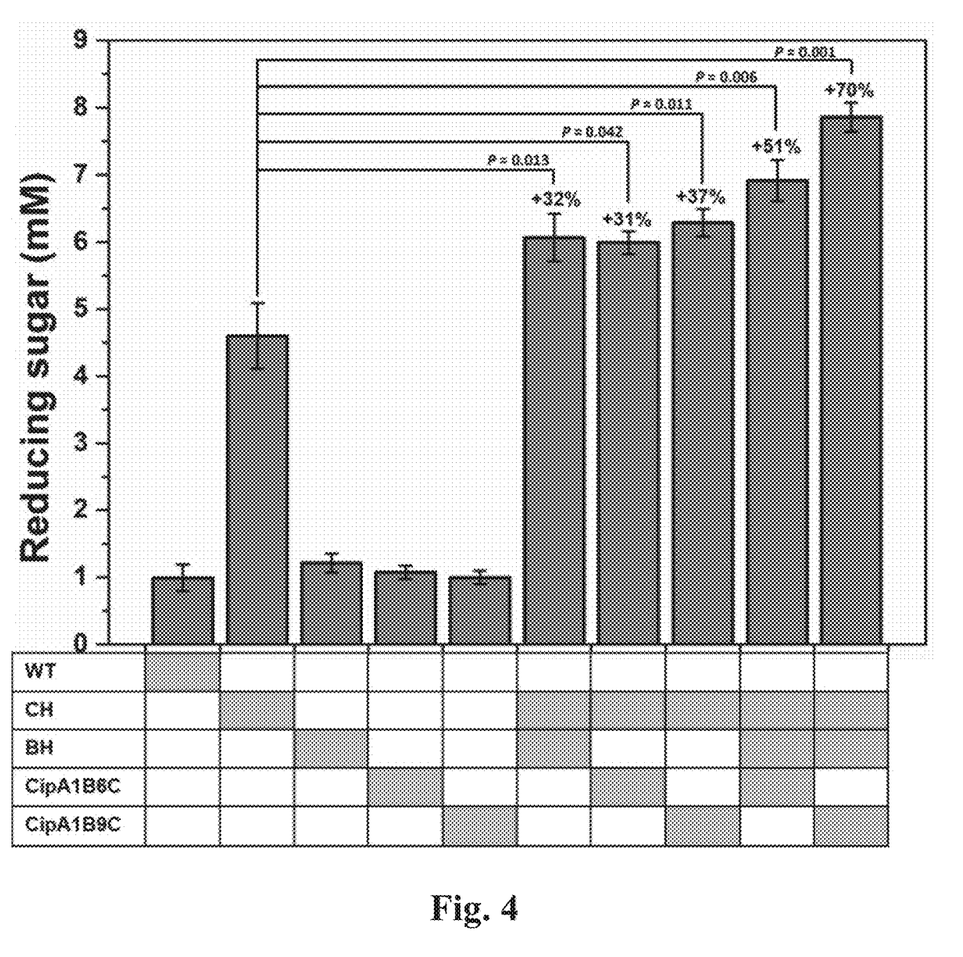
FIG. 4. Effects of cellulase booster on cellulosome complex. Cellulase host (CH), booster host (BH) and CipA variants were cultured separately and condensed supernatants were used for the experiment. The supernatants of 4G5 wild type (WT), CH-17, BH-20 and CipA (1B6C or 1B9C) were mixed in the ratio of 10:2:2 and allowed to form complexes, which were then mixed with avicel. The reducing sugar release was determined by the DNS method. The results are expressed as mean (n=3)±standard deviation (SD). P values were determined using two-tailed Student t-tests.

A cellulase host (CH) was constructed by electroporating equimolar ratios of CBHII-t, TrEgIII-t, and NpaBGS-t genes into K. marxianus 4G5. The transformants were selected on YPG plates supplemented with hygromycin. The transformants integrated with all of the cellulase genes were selected by PCR screening, and their activity was confirmed by enzyme assays. Transformant CH-17 showed the highest enzyme activity and released 2.84 mM and 2.91 mM reducing sugars from avicel and filter paper, respectively. Similarly, to demonstrate the effects of the cellulase booster, TaLPMO-t and MtCDH-t genes were transformed into K. marxianus 4G5 (booster host: BH) and the booster functionality was confirmed by measuring the $H_2O_2$ production using the Amplex red/HRP assay kit. The production of $H_2O_2$ is directly proportional to the LPMO activity, which requires enzymatic (CDH together with cellobiose) or non-enzymatic (ascorbate) electron donors. Hence, the enzyme activity was assayed using two kinds of electron donors: cellobiose and ascorbate. The transformant BH-20 released 1.60 μM and 12.13 μM of $H_2O_2$ using the substrate cellobiose and ascorbate, respectively. The lowest $H_2O_2$ production was observed while using cellobiose as the substrate, and its concentration was increased in a time-dependent manner. In this case, CDH needs to oxidize the cellobiose and transfer an electron through its heme domain to LPMO (Phillips et al. *ACS Chem Biol* 6, 1399-1406 (2011)). In contrast, ascorbate can directly donate the electron to LMPO, thereby producing higher quantities of $H_2O_2$ in a short time. Boosting effects of cellulase boosters The selected booster host BH-20, which expresses TaLPMO-t and MtCDH-t, and the selected cellulase host CH-17, which expresses CBHII-t, TrEgIII-t, and NpaBGS-t, were cultured separately. Then the condensed supernatants of CH-17 and BH-20 were mixed at three different ratios (10:1, 10:2 and 10:3) and incubated along with avicel. The addition of CH-17 supernatant to the BH-20 supernatant at the ratio of 10:2 increased the soluble sugar release by 31%, confirming that LPMO has a proper function in K. marxianus. Similarly, the effects of cellulase boosters on the cellulosome complex were examined by mixing the supernatants of CH-17, BH-20 and CipA variants (including 1B3C, 1B6C, 1B9C, 0B9C, or 2B9C) in the molar ratio of 10:2:2 (CH:BH:CipA) and the enzyme mix was allowed to form the cellulosome complex at 37° C. Avicel was added to the cellulosome complex and reducing sugar release was measured. The results showed that the activity of the cellulase host improved by 32% (6.07 mM) with cellulase boosters, and the addition of CipA 1B6C or CipA 1B9C along with CH-17 increased the sugar release by 30% and 36%, respectively (FIG. 4). Importantly, the addition of CH-17 and BH-20 supernatants together with either CipA 1B6C or 1B9C increased the sugar release by 51% and 70%, respectively. These results corroborate the effects of cellulase boosters on the cellulosome complex. Therefore, a new host was constructed, called Enzyme Host (EH), with three cellulases (TrEgIII-t, CBHII-t, and NpaBGS-t) and two cellulase boosters (TaLPMO-t and MtCDH-t). Transformants with all the integrated genes were selected, and their expression was confirmed by qPCR analysis using actin as a reference gene. Transformant EH-P1-44 demonstrated the highest enzyme activity and released 4.55 mM and 4.97 mM of reducing sugar from avicel and filter paper, respectively.

Effects of cohesin and CBM numbers on cellulosome efficiency

Figure 5:
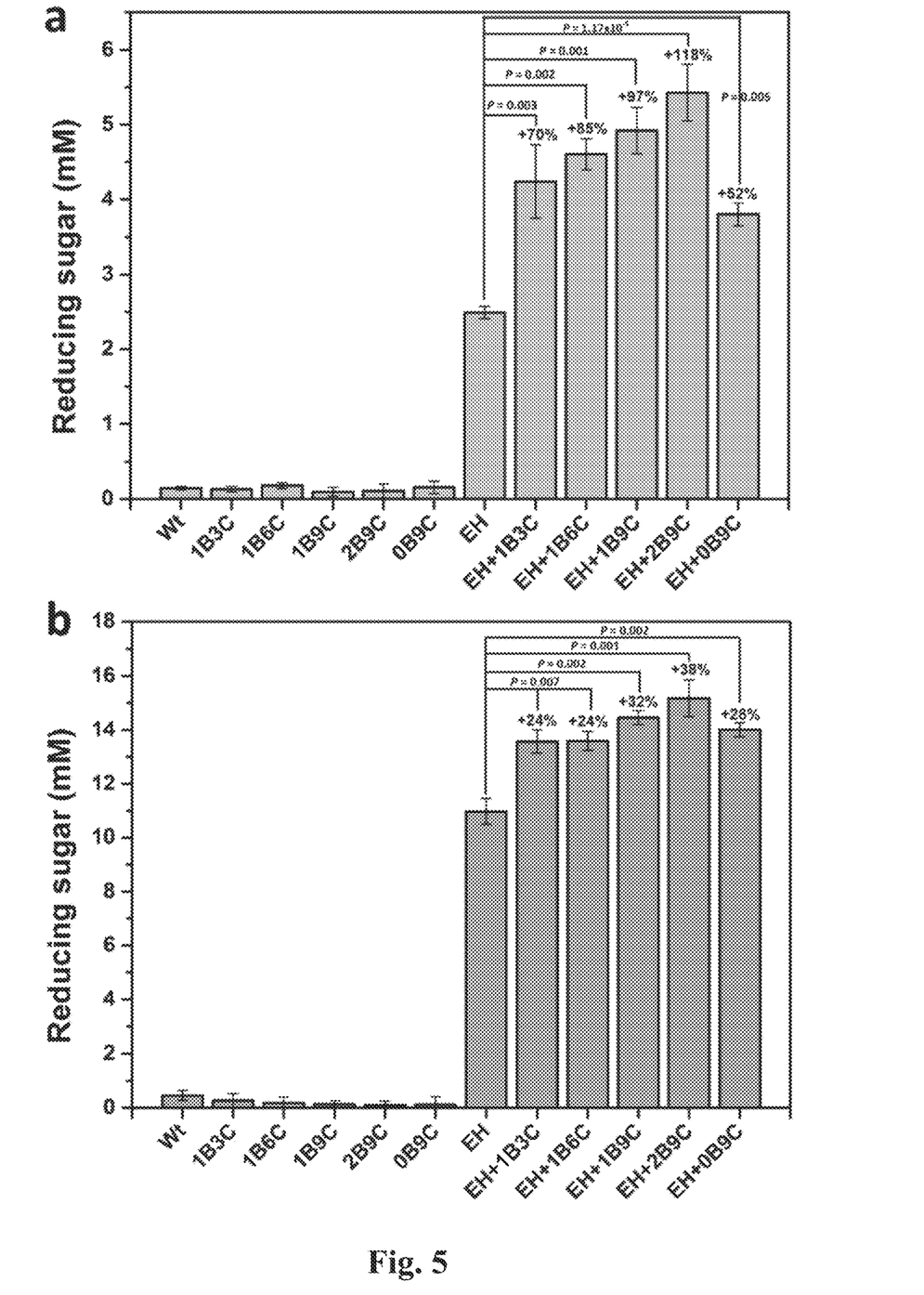
FIG. 5. Effects of CipA variants on avicel (a) and PASC (b) degradation. Wild type (WT), Enzyme host (EH-P1-44) and CipA variants (1B3C, 1B6C, 1B9C, 0B9C and 2B9C) were cultured separately and condensed supernatants were used for the experiment. The enzyme host (EH) and CipA were mixed in the ratio of 10:2 and allowed to form complexes, which were then mixed with avicel or PASC. The reducing sugar release was measured using the DNS method. The results are expressed as mean (n=3)±standard deviation (SD). P values were determined using two-tailed Student t-tests.

The effects of cohesin and CBM numbers on sugar release were assayed using avicel or phosphoric acid-swollen cellulose (PASC) as the substrate. The condensed supernatant of EH-P1-44 (expressing CBHII-t, TrEgIII-t, NpaBGS-t, TaLPMO-t and MtCDH-t) and the hosts expressing CipA variants were mixed at different ratios (10:1, 10:2 and 10:3). After the complex formation at 37° C., substrates were added to the mixture and sugar release was measured following 48 h incubation at 37° C. The data exhibited a tremendous increase in enzyme activity when the EH-P1-44 supernatant was mixed with CipA variants at the ratio of 10:2. CipA 2B9C exhibited the highest increase in sugar release, 118%, followed by 97%, 85% and 70% increases for CipA 1B9C, CipA 1B6C, and CipA 1B3C, respectively (FIG. 5a). These data indicate that the cohesin number has a strong influence on sugar release, especially when using avicel as the substrate. However, when PASC was used as the substrate, the influence of the cohesin number was less significant (FIG. 5b). The addition of CipA 1B9C, CipA 1B6C, or CipA 1B3C only increased 32%, 24%, or 24% in the sugar release compared to the activity of EH-P1-44 alone (FIG. 5b). These results substantiate the vital role of the cohesin number in enzyme synergism, which is important for digesting complex substrates (i.e., microcrystalline cellulose or plant biomass).

Figure 6:
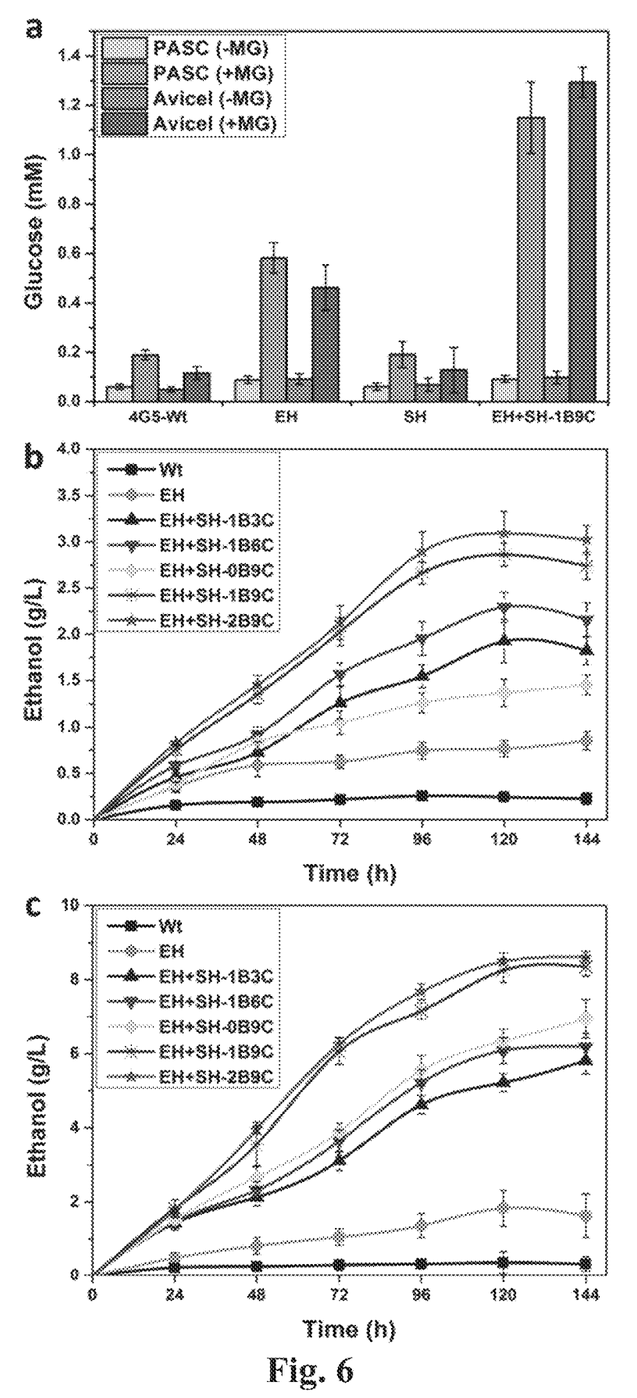
FIG. 6. Hydrolysis of avicel or PASC and production of glucose or ethanol by the engineered cellulosome. (a) Analysis of glucose release from avicel or PASC. The cells were pre-cultured and 10 O.D. cells were inoculated into YP medium supplemented with 1% avicel or PASC with or without 100 mM methylglyoxal (MG). In the presence of MG, the glucose metabolism of host cell was arrested, while the glucose produced during the hydrolysis remained intact. (b & c) Time course of cellulosic ethanol production by yeast consortium composed of enzyme host (EH-P1-44) and scaffold host SH-1B3C, SH-1B6C, SH-0B9C, SH-1B9C or SH-2B9C at the optimized ratio of 10:1. Ethanol production from 10 g/L avicel (b) or 20 g/L PASC (c) was analyzed using HPLC.

The number of CBMs also plays an important role in the efficiency of the cellulosome complex because they bring the entire complex towards the substrate. The data for sugar release from avicel showed that the construct with two CBMs (CipA 2B9C) remarkably increased the sugar release by 118%, followed by 97% for CipA with one CBM. Although CipA without any CBM increased the sugar release by 52%, it was the lowest among all the tested CipA variants (FIG. 5a). However, the number of CBMs did not significantly improve the sugar release from PASC. The CipA 2B9C exhibited 38% increased sugar release, whereas CipA 1B9C and CipA 0B9C increased the sugar release by 32% and 28%, respectively (FIG. 5b). These results confirm the significance of the CBM on a synthetic scaffold for microcrystalline cellulose degradation. Demonstration of consolidated bioprocessing Consolidated bioprocessing (CBP) is a single-process approach that includes the production of cellulase enzymes, biomass saccharification and fermentation, and could be an ideal approach to cellulosic ethanol production. The hydrolytic activity of cellulosome on cellulosic substrates was demonstrated with and without methylglyoxal, a glucose metabolism inhibitor. Cells were cultured in YP containing 1% avicel or PASC supplemented with or without 100 mM methylglyoxal for 6 h. The lowest amount of glucose was observed in all conditions in the absence of methylglyoxal (FIG. 6a). The concentration of glucose increased tremendously in the presence of 100 mM methylglyoxal. Notably, EH-P1-44 along with Scaffold Host (SH) released a higher amount of glucose using avicel than PASC as the substrate. This confirms the above observation that the scaffold increased the cellulolytic activity on microcrystalline cellulose.

For efficient secretion and assembly of the cellulosomal protein complex, the EH-P1-44 host and the SH-1B9C host expressing CipA 1B9C and OlpB were co-cultured in different ratios, and their ethanol-producing ability was analyzed using avicel. The direct ethanol fermentation was conducted under a microaerobic condition to provide the oxygen required for LPMO activity. The microaerobic condition was achieved by culturing the cells with 5% headspace in 50 ml serum bottles. The maximal ethanol production (2.68 g/L) was achieved on avicel when the EH-P1-44 and SH-1B9C hosts were co-cultured at the ratio of 10:1. The cellulosic ethanol production rates of SH-CipA variants (1B3C, 1B6C, 0B9C, 1B9C and 2B9C) along with EH-P1-44 were investigated to show the influences of CBM and cohesin numbers on enzyme-substrate-microbe complex synergism. As shown in FIG. 6b, when using avicel as the substrate, the maximum ethanol production (3.09 g/L) was achieved in the consortium that contained EH-P1-44 and SH-2B9C. In comparison, EH-P1-44+SH-1B9C and EH-P1-44+SH-0B9C produced 2.86 g/L and 1.37 g/L of ethanol, respectively. Cellulosome hosts expressing 1B3C and 1B6C produced 1.93 and 2.29 g/L of ethanol, which are higher than the full scaffold without the CBM (0B9C). These observations indicate that the number of CBMs had a strong influence on ethanol production using microcrystalline cellulose. In contrast, while using PASC as the substrate, EH-P1-44+SH-1B9C and EH-P1-44+SH-2B9C produced similar quantities of ethanol, i.e., 8.25 g/L and 8.49 g/L, respectively (FIG. 6c). Interestingly, when PASC was used as the substrate, the ethanol titer of the consortium containing SH-0B9C cells (lacking CBM) was higher (6.95 g/L) than the cellulosomes containing SH-1B3C and SH-1B6C (5.81 g/L and 6.91 g/L, respectively).

In terms of ethanol production, the mini-cellulosome engineered by Fan et al. (*Natl Acad Sci USA* 109, 13260-13265 (2012)), which could display up to 12 enzymes, produced 1.41 g/L and 1.09 g/L of ethanol from avicel and PASC, respectively. By including the LPMO and CDH genes in the cellulosome, Liang et al. (*Appl Environ Microbiol* 80, 6677-6684 (2014)) improved the ethanol titer to 1.5 g/L and 2.7 g/L for avicel and PASC, respectively. Compared to Liang et al."s study, the present disclosure achieved two-fold higher ethanol production (3.09 g/L) using avicel and three-fold higher ethanol production (8.61 g/L) using PASC as the sole carbon source (FIGS. 6b and 6c).

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

sylphosphatidylinositol (GPI) domain of *Saccharomyces cerevisiae*, wherein the recombinant protein is free of tandem repeats of SEQ ID NO: 1 (TPSDEP).

2. The recombinant protein according to claim 1, wherein the GPI domain of the recombinant protein is linked to a cell membrane-anchored protein.

3. A recombinant cellulosome complex comprising:
the recombinant protein according to claim 1;
a recombinant cellulosome complex integrating protein A (CipA) comprising a plurality of type I cohesin repeats of *C. thermocellum*, at least two cellulose-binding modules of *C. thermocellum* and a type II dockerin of *C. thermocellum*; and
a plurality of recombinant enzymes each comprising a type I dockerin of *C. thermocellum*, wherein the recombinant enzymes are endoglucanase TrEgIII, exoglucanase CBHII or β-glucosidase NpaBGS.

4. The recombinant cellulosome complex according to claim 3, which further comprises a lytic polysaccharide monooxygenase TaLPMO.

5. The recombinant cellulosome complex according to claim 3, which further comprises a recombinant cellobiose dehydrogenase MtCDH.

6. An isolated recombinant host cell expressing the recombinant cellulosome complex according to claim 3.

7. The isolated recombinant host cell according to claim 6, wherein the recombinant protein further comprises a GPI domain of *S. cerevisiae*, and the isolated recombinant host cell expresses the recombinant protein or the recombinant cellulosome complex on the surface of the isolated recombinant host cell.

8. The isolated recombinant host cell according to claim 6, which is a yeast cell.

9. The isolated recombinant host cell according to claim 6, wherein the recombinant protein or the recombinant cellulosome complex is encoded by the genome of the isolated recombinant host cell.

10. A method for digesting a cellulose, comprising contacting cellulose with the recombinant cellulosome complex according to claim 3.

11. The method according to claim 10, wherein the cellulose is a microcrystalline cellulose.

12. The method according to claim 10, wherein the cellulose is converted into reducing sugars or ethanol.

13. A method for producing ethanol, comprising the method according to claim 10.

14. The recombinant cellulosome complex according to claim 3, wherein the recombinant CipA comprises 2, 3, 4, or 5 cellulose-binding modules.

What is claimed is:

1. A recombinant protein comprising a plurality of type II cohesin repeats of *Clostridium thermocellum* and a glyco- 15. The recombinant cellulosome complex according to claim 3, wherein the type I dockerin is fused at C-terminus of endoglucanase TrEgIII and exoglucanase CBHII.

16. The recombinant cellulosome complex according to claim 3, wherein the type I dockerin is fused at N- or C-terminus of β-glucosidase NpaBGS.

\* \* \* \* \*

SEQUENCE LISTING

<160> NUMBER OF SEQ ID NOS: 1

<210> SEQ ID NO 1
<211> LENGTH: 6
<212> TYPE: PRT
<213> ORGANISM: Clostridium thermocellum

<400> SEQUENCE: 1

Thr Pro Ser Asp Glu Pro
1               5